United States Patent [19]

Cebrian

[11] 4,046,919
[45] Sept. 6, 1977

[54] TREATMENT OF CELLS

[75] Inventor: Gregorio Ramon Cebrian, Madrid, Spain

[73] Assignee: Fundacion de Estudios Farmaco-Biologicos, Madrid, Spain

[21] Appl. No.: 543,910

[22] Filed: Jan. 24, 1975

Related U.S. Application Data

[60] Division of Ser. No. 366,360, June 4, 1973, Pat. No. 3,991,211, which is a division of Ser. No. 201,331, Nov. 23, 1971, abandoned, which is a continuation-in-part of Ser. No. 155,239, June 21, 1971, abandoned.

[30] Foreign Application Priority Data

June 19, 1970 Spain ............................. 380951
Dec. 30, 1977 United Kingdom ............... 61899/70

[51] Int. Cl.² .......................................... A61K 31/075
[52] U.S. Cl. .................................................. 424/338
[58] Field of Search ....................................... 424/338

[56] References Cited

PUBLICATIONS

Zobrist et al. – Chem. Abst. vol. 71 (1969) p. 105214s.
Weitzel et al. – Chem. Abst. vol. 57 (1962) p. 1492b.

*Primary Examiner*—Sam Rosen
*Attorney, Agent, or Firm*—Wenderoth, Lind & Ponack

[57] ABSTRACT

Method of treating virus disorders by administering certain compounds, such as benzoyl peroxide, into the blood. Entry of these compounds into the sick cells results in, because of the pH and redox-potential conditions in those cells, oxidation phenomena and deposition of an antiseptic substance in the sick cells, thereby causing cellular aging and necrosis.

5 Claims, No Drawings

TREATMENT OF CELLS

This application is a division of application Ser. No. 366,360, filed June 4, 1973, now U.S. Pat. No. 3,991,211 which in turn is a division of application Ser. No. 201,331, filed Nov. 23, 1971, now abandoned, which in turn is a continuation-in-part of application Ser. No. 155,239, filed June 21, 1971, now abandoned.

The present invention relates to a process and a preparation for combatting or treating diseases caused by vira or mycoplasma, especially neoformations, which process and preparation are based on a new principle for combatting viruses.

This principle is based on the fact that the chemical and physico-chemical conditions with regard, inter alia, to pH-value and redox-potential in sick cells are different from conditions in the sound cells. The principle consists in administering to the patient one or more chemical substances of no or only insignificant toxicity which will, solely in the sick cells, or predominantly in the sick cells, owing to these special conditions, be transformed, thereby giving rise to substances preventing the growth of the virus, whether by interferring directly in the virus reproduction processes or by killing the sick cells, so that a selective abiotic environment is produced.

For the present, the inventor has particularly concentrated upon bringing about processes which 1. result in the production of oxidation phenomena or an oxidizing potential in the cells attacked, for instance development of nascent oxygen or hydrogen peroxide, or
2. result in the formation of one or more substances having an antiseptic activity, which are left as a residue in the cells attacked, or which result in both these states.

The substances which the inventor has been interested in are substances which decompose at a pH below 7, since acid conditions are prevailing in cells attacked by viruses and, in most cases, in cells attacked by mycoplasma, such as in tumor cells.

A number of substances have been investigated and submitted to thorough tests. The inventor has succeeded in proving that the substances mentioned below, administered in the manner described, possess therapeutic activity and have no side effects. All of the substances cause the production of oxidation phenomena as well as the formation of an antiseptic residue.

SUBSTANCE 1

1,2-Diphenyl-α,β-diketone superoxide, also called benzoyl peroxide.

Formula

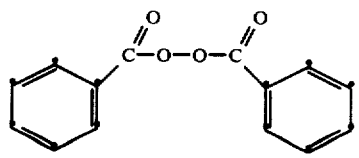

SUBSTANCE 2

1,2-Diphenyl-α,β-diketone, also called dibenzoyl, diphenyl-glyoxal and 1,2-diphenylethanedione.

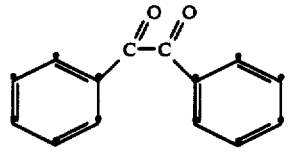

SUBSTANCE 3

Phenolphthalein, also called 3,3-bis(p-hydroxyphenyl)-phthalide and α-(p-hydroxyphenyl)-α-(4-oxo-2,5-cyclohexadien-1-ylidene)-o-toluic acid, or the sodium salt thereof.

Formula

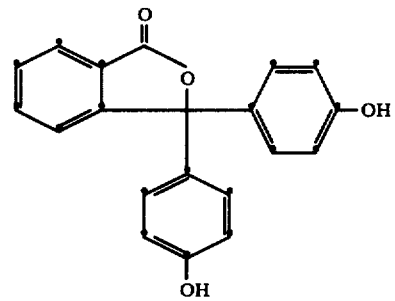

or the sodium salt thereof, i.e.

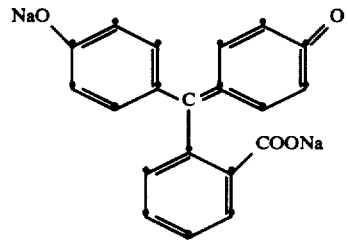

It must be understood that, although only a few specific compounds useful in the method of the present invention have been mentioned, any substance which is capable of performing the same function as those compounds specifically mentioned is acceptable. Thus, those substances which (a) are non-toxic and do not produce harmful side-effects, (b) are oxidants at a pH less than 7 and stable under slightly alkaline conditions and (c) because of the pH and redox-potential conditions in the altered cells, exercise a selective oxidizing effect on the altered cells and deposit an antiseptic substance in the cells, possibly accompanied by the release of nascent oxygen, are acceptable. These substances are all acceptable because, if they do satisfy all these conditions, they ultimately cause the cells to age and thereby advance necrosis.

It has been found that the best way of obtaining contact between the active substances and the sick cells in which virus-reproducing, and other processes which are to be controlled, are taking place, is internal administration, i.e., administration in such a manner that the active substances are brought into the blood. The substances may be directly introduced into the blood or absorbed in the blood through the lymphatic system, whereby all sites within the organism which might be attached are reached.

It has been found to be of importance that the substances are administered in the form of solutions in liposoluble media, such as, for example, oils or fatty acid esters or, in intravenous administration, with, for example polyethylene glycol. These solutions can, of course, contain the usual adjuvants used in pharmacy, such as antiseptics, viscosity-controlling substances, wetting agents, local anesthetics (in preparations for injection), solubilizers, etc.

To summarize, the invention in one aspect resides in a preparation for the treatment of diseases caused by vira or mycoplasma, as well as in neoformations, consisting of a solution, in a liposoluble medium suitable for internal administration, of one or more organic chemical compounds having no or insignificant toxicity, which compounds are capable of, at a pH below 7, undergoing chemical transformation, thereby giving rise to oxidation phenomena.

An especially advantageous preparation consists of a solution as mentioned above containing a substance or substances which by chemical transformation, besides causing oxidation phenomena, form an antiseptic which produces an abiotic selective zone.

Three dispensing forms for the substances 1-3 have been prepared, whereby the substances are caused to circulate in the blood and produce the desired effect: agents for peroral use, agents for injection (intramuscular, hypodermic or intravenous) and suppositories. By these modes of administration the substances are brought into the blood and reach all the diseased areas.

Hereinafter follows a detailed description of the production of preparations containing both the substances 1 and 2 in dissolved form, for oral and parenteral administration, and for administration in the form of suppositories, and of preparations containing the substance 3 in dissolved form, intended for injection. It is to be understood, however, that substances 1 and 2 may be used individually, i.e., without admixture with one another.

Preparations Containing the Substances Nos. 1 and 2

Use is made of, as solvents, oil or ethyl oleate, both having as little acidity as possible. It must be an oil of good quality or an ethyl oleate having the properties prescribed by the different pharmacopoeiae.

Furthermore, use is made of, as a solvent, polyethylene glycol (M.W. 200), also called plioxyethylene glycol (200), Macrogol 200 and PEG 200 of the formula $CH_2(OH).(CH_2O.CH_2)_m.CH_2OH$, where $m$ is 3 or 4. The molecular weight of the substance varies between 185 and 225. Specific gravity is 1.12. It is a clear liquid, colorless, viscous and having a characteristic faint odor. It is soluble in water, alcohol, acetone and in other glycols. It is insoluble in ether and aliphatic hydrocarbons, but soluble in aromatic hydrocarbons.

Use may also be made of other substances possessing properties similar to those of the indicated three solvents.

Preparation for Peroral Administration

The production method is as follows, with the natural margin of variations allowable for such preparation:

Oil (any which is physiologically acceptable) or ethyl oleate is heated to about 80° C, and under vigorous stirring, from 1 to 4 g % w/v, e.g. 2 g %, of substance No. 2 and afterwards, from 0.5 to 2 g % w/v, e.g. 1 g %, substance No. 1 (dried) are added.

Stirring for about 15 minutes at 80° C is sufficient to dissolve both substances. When the solution is cooled, it is ready for use as a peroral drug. If desired, it can be enclosed in capsules.

It should be observed that if the mixture is heated to, e.g. 70° C, instead of 80° C, the dissolution still takes place, but in such case stirring for much longer time than 15 minutes is required.

Preparation for Intramuscular or Hypodermic Injection a. A solution as the one described above for oral administration can, in a cooled state, and in a lower dosage, e.g. from 0.5 to 2 g % w/v, e.g. 1 g %, of both substances 1 and 2, with 3% benzyl alcohol being added under mechanical stirring, be used a few days, e.g. 4 or 5 days later for intramuscular or hypodermic injection.

b. From 0.5 to 1.5 g % w/w, e.g. 1 g %, of 1.2-diphenyl-$\alpha,\beta$-diketone is dissolved in polyethylene glycol (200), heated to 80° C, under mechanical stirring and immediately afterwards, still at the same temperature, from 0.5 to 1.5 g % w/w, e.g. 1 g %, 1,2-diphenyl-$\alpha,\beta$-diketone superoxide is added and dissolved.

When the substances are dissolved, five minutes being sufficient, the solution is allowed to cool, and when cold, about 3% w/w of benzyl alcohol is added under vigorous stirring.

This solution, filtered and bottled in capped vials or ampoules, can four-five days later be used as an injectable solution for hypodermic or intramuscular injections. This solution should be kept at temperatures between 0° and 5° C until ready for use.

The above-mentioned solution can also be prepared at room temperature under stirring even with a greater concentration of the active substances, the stirring being carried out for a much longer period of time, e.g. 2 hours. The solution is kept in cold storage for subsequent aseptic bottling.

Preparation for Intravenous Administration

A mixture of polyethylene glycol (200) and half again as much of Tween 80 (polyoxyethylene sorbitol monooleate) is prepared. To this mixture is added 1% w/w of the sodium salt of dioctyl sulfosuccinic acid, and under mechanical stirring there is added to this viscous liquid from 0.2 to 2 g % w/w, e.g. 1 g % of 1,2-diphenyl-$\alpha,\beta$-diketone superoxide and from 0.2 to 2 g % w/w e.g. 1 g %, of 1,2-diphenyl-$\alpha,\beta$-diketone, the order in which the two substances are added making no difference as long as dissolution is effected. 24 hours later (continuous stirring is not necessary, but the mixture should be stirred intermittently), 3 % w/w of benzyl alcohol is added and the liquid is then ready for aseptic bottling in injection ampoules. Both the non-bottled liquid and the injection ampoules are kept in cold storage.

Propylene glycol, vegetable oils and ethyl oleate may also be used in the preparations for intravenous administration.

Preparation for Use as Suppositories

As a basic mass use can be made of cocoa butter or a synthetic mass such as monolenes, witepsol, etc. In all cases the mass is heated to 80° C, and under mechanical stirring there is added from 1 to 4 g % w/w, e.g. 2 g %, of 1,2-diphenyl-$\alpha,\beta$-diketone and afterwards from 0.5 to 2 g % w/w, e.g. 1 g %, of 1,2-diphenyl$\alpha,\beta$-diketone superoxide, the temperature being maintained at 80° C. When these substances are dissolved (occurs after stirring for about a quarter hour), the mass is allowed to cool and the suppositories can then be prepared.

Among the above products, cocoa butter is, as known, a natural product prepared on the basis of vegetable fatty acid esters, saturated or unsaturated, with glycerol. Witepsol is a synthetic product, a vegetable fatty acid ester, saturated, with an even number of carbon atoms, with glycerol.

In conformity with that mentioned above, the solution forming the basis of the suppositories may be prepared at a lower temperature, but with a longer stirring period.

The suppositories are to be kept in cold storage until ready for use.

It is also possible to administer the suppositories orally, giving them an appropriate shape.

Preparations Containing Substance No. 3

Preparation for Hypodermic or Intramuscular Injection

Polyethylene glycol (200) or propylene glycol is heated to 80° C, and under mechanical stirring from 1 to 10% w/w, e.g. 5% of phenolphthalein is dissolved therein. When it is dissolved, the mixture is allowed to cool and, under stirring, 3% w/w of benzyl alcohol is added, whereafter the liquid is ready for aseptic bottling in capped vials or ampoules and can be used three or four days later.

Preparation for Intravenous Administration

A mixture of polyethylene glycol (200) and half again as much of Tween 80 (polyoxyethylene sorbitol monooleate) is prepared. 1% w/w of the sodium salt of dioctyl sulfosuccinic acid is added to the mixture and under continuous stirring there is added to this viscous liquid from 0.4 to 4% w/w, e.g. 2%, of phenolphthalein until this is dissolved. After adding to this mixture 3% w/w of benzyl alcohol, a liquid is obtained which, after filtering and aseptic bottling in ampoules, can be used for intravenous injections.

In all viral processes, the recommended dosage is the administration of three fatty cores (suppositories via oral means), 4 times a day at meal times: breakfast, lunch, mid-afternoon meal and dinner.

In grave cases, treatment is initiated administering, in addition to the fatty cores, a daily subcutaneous injection in deep fatty areas of 4 c.c., for instance during one month.

In case of influenza, it is sufficient to administer a suppository in the morning and at night, during 1 to 3 days.

It is assumed that the mechanism of action of the above mentioned three substances is the following, but the invention is not bound to the correctness of such mechanism:

Substance No. 1

This substance is, as mentioned, led in to the blood, directly or through the lymphatic system. In the blood at normal pH the substance is stable and circulates dissolved through the organism. When the substance reaches the sick cells - in the metabolism of which unusually much lactic acid is present - or, in other words, zones of acid pH, the substance liberates nascent oxygen which oxidizes in situ, and simultaneously benzoic acid is produced, which is deposited in the cells.

Substance No. 2

This substance is also led into the blood, directly or through the lymphatic system. In certain abnormal cells, such as for example in viruses focii, the substance is by molecular exchange converted into diphenylglycolic acid which then, in these abnormal cells, is converted into diphenylacetic acid according to the following:

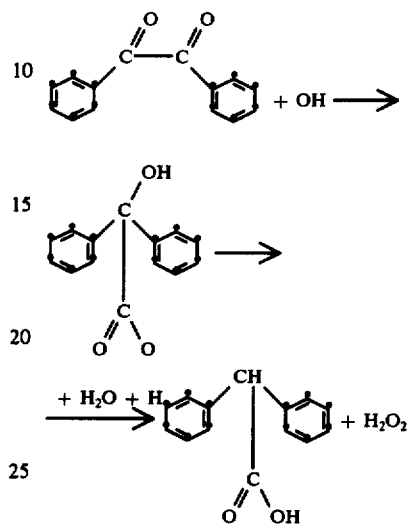

This reaction sequence is supported by the fact that it has been ascertained that an oxidation takes place and that diphenylacetic acid is deposited in the cells.

Substance 3

This substance circulates in dissolved state in the blood,

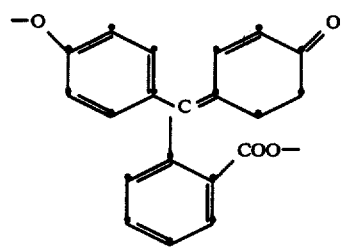

and when it reaches cells having acid zones, liberates

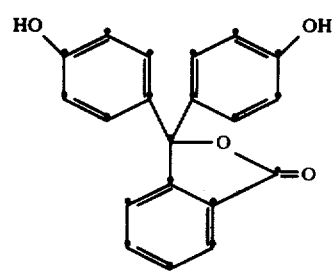

which is more insoluble than the sodium salt. It is strongly antiseptic because of its OH-groups and at the same time possesses oxidizing properties, it being eliminated in the form

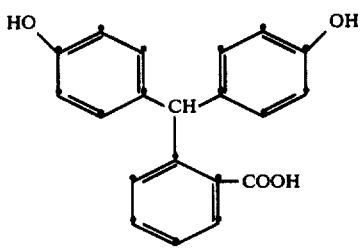

i.e., 4',4''-dihydroxy triphenylmethane-2-carboxylic acid.

It is considered that the substances 1-3 interfere in the virus reproduction processes by destroying, by oxidation, certain components necessary for building up, having a free amino group or free guanidino group, e.g. lysine,

which has a free ε-NH$_2$ group, and arginine

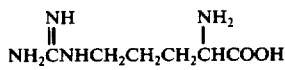

which has a free δ-guanidino group. In support of this, it has been found that histamine in situ at slightly alkaline pH, even at pH 7, is destroyed in a short period of time by oxidation.

It is important to realize that through the use of substances 1-3, or corresponding products, a process of focal necrosis can be produced in test tumors treated with these substances, a necrosis which is localized to focii and prevents the spreading of viruses.

Preparations containing the described substances have been thoroughly tested with regard to their possible toxicity as well as their therapeutic activity.

With toxicity tests, it has been ascertained that the substances are non-toxic. They cause neither tissue alterations nor embryopathic alterations. They do not alter either the circulatory function, nor the electrocardiogram or electroencephalogram. The substances cause no change in the blood picture and they do not change the normal analysis figures. No renal disturbances occur. They are therefore, no contra-indications or side effects which might prevent use of the substances, whether for short- or long-term treatments.

With clinical experiments, surprising results have been achieved within the field of veterinary medicine, e.g. in the treatment of poultry leukosis, foot-and-mouth disease in cows, bulls and pigs and viral abortion in sheep and enzootic pneumonia in pigs and calves, caused by mycoplasma, and also within human medicine, in the treatment of, for example, influenza, hepatitis, herpes zoster, rubeola (measles), parotitis (mumps), sclerosis in plates, and in general all kinds of viral processes, even warts (i.a. verrucae plantares).

The best results hitherto have been obtained with preparations containing a combination of substances 1 and 2.

Clinical experiments have been carried out with these preparations at the Veterinary Clinic of the Veterinary Faculty in Madrid by Prof. Felix Sanz Sanchez. A great many experiments relating to poultry leukosis, with blank determination, were carried out on poultry stock controlled according to regulations with several batches of from 15,000 to 20,000 chickens. The preparation was mixed with the feed, always with satisfactory results. Identical experiments dealing with the treatment of foot-and-mouth disease in cows, as well as in bulls reared for bull-fighting, and in pigs, were carried out, the preparation being used as an injection or mixed with fodder. Recovery was always noticed during the first few days treatment. In viral pneumonia therapy for pigs and calves, the employment of the preparation for injection has proved to be definitely therapeutic, since one injection has been enough to result in complete cure. In the case of viral abortion in sheep, a single injection solved the problem.

The amazing effects observed in the experiments and the distinct anti-viral effect encouraged almost inevitably testing of the preparations in human antiviral medicine. Tests were begun on a larger scale with oral application of the preparations for combatting influenza, with excellent results.

The substances 1-3 can be prepared by the usual methods. Substance 1 can, for example, be prepared by reaction between benzoyl chloride and a cooled solution of sodium peroxide, cf. A. I. Vogel, *Practical Organic Chemistry*, 3rd ed. (Longmans, London, 1954), p. 807; Gattermann-Wieland, *Praxis des Organischen Chemikers*, 40th ed. (de Gruyter, Berlin, 1961) p. 115.

Substance 2 can be prepared by the oxidation of benzoin with HNO$_3$ or with a copper sulfate-pyridine mixture, cf. e.g. Adams, Marvel, Org. Syn. vol. I. p. 25 (1921); Clarke, Dreger, ibid. coll. vol. I, 80 (87, sec.ed.); Hatt, Pilgrim, Hurran, *J. Chem. Soc.* 1936, 93. L. F. Fieser, *Experiments in Organic Chemistry*, 3rd ed. (Boston, 1955), p. 173; *Organic Experiments* (Boston, 1964), p. 214.

Substance 3 can be prepared by condensing phenol with phthalic anhydride in presence of dehydrating agents such as zinc chloride, sulfuric acid, toluenesulfonic acid: Baeyer, Ann. 202, 69 (1880); Herzog, Chem. Ztg. 51, 84 (1927); Hubacher, U.S. Pat. No. 2,192,485; Gamrath, U.S. Pat. No. 2,522,939.

I claim:

1. A method for selective cell necrosis, which comprises administering through the circulatory system to the altered cells of a patient having such altered cells a pharmaceutically effective amount of a composition containing benzoyl peroxide and a pharmaceutically suitable carrier therefor.

2. The method according to claim 1, wherein the administration is perorally and the composition is prepared by mixing an oil or ethyl oleate, with low degree of acidity, and benzoyl peroxide under stirring at a temperature between ambient temperature and 80° C to dissolve the mixture, the proportion of benzoyl peroxide being between 0.5 and 2% w/v, and allowing the resultant mixture to cool.

3. The method according to claim 1, wherein the administration is intramuscularly or by hypodermic injection and the composition is prepared by mixing an oil or ethyl oleate with benzoyl peroxide under stirring at a temperature between ambient temperature and 80° C to dissolve the mixture, the proportion of benzoyl peroxide being between 0.5 and 1.5% w/v, cooling the solution, adding 3% w/w of benzyl alcohol under stirring, and permitting the solution to stand for four or five days before use.

4. A method for selective cell necrosis, which comprises administering into the blood of a patient affected with altered cells a pharmaceutically effective amount of benzoyl peroxide in the form of a solution in a pharmaceutically acceptable liposoluble medium suitable for internal administration.

5. A composition for achieving selective cell necrosis, comprising benzoyl peroxide and a pharmaceutically acceptable liposoluble medium, as carrier, suitable for internal administration.

* * * * *